(12) United States Patent
Renshaw

(10) Patent No.: US 7,737,128 B2
(45) Date of Patent: Jun. 15, 2010

(54) PYRIMIDINES, SUCH AS URIDINE, IN TREATMENTS FOR PATIENTS WITH BIPOLAR DISORDER

(75) Inventor: Perry Renshaw, Salt Lake City, UT (US)

(73) Assignee: The McLean Hospital Corporation, Belmont, MA (US)

( * ) Notice: Subject to any disclaimer, the term of this patent is extended or adjusted under 35 U.S.C. 154(b) by 124 days.

(21) Appl. No.: 11/629,111

(22) PCT Filed: Jun. 10, 2005

(86) PCT No.: PCT/US2005/020690

§ 371 (c)(1),
(2), (4) Date: Oct. 10, 2008

(87) PCT Pub. No.: WO2005/122767

PCT Pub. Date: Dec. 29, 2005

(65) Prior Publication Data

US 2009/0054370 A1 Feb. 26, 2009

Related U.S. Application Data

(60) Provisional application No. 60/578,885, filed on Jun. 10, 2004.

(51) Int. Cl.
*A01N 43/04* (2006.01)
*A61K 31/70* (2006.01)

(52) U.S. Cl. .............................. 514/50; 514/42; 514/43; 514/49

(58) Field of Classification Search ........................ None
See application file for complete search history.

(56) References Cited

U.S. PATENT DOCUMENTS

| 4,027,017 | A | 5/1977 | Hata et al. |
|---|---|---|---|
| 4,048,316 | A | 9/1977 | Penn |
| 4,115,576 | A | 9/1978 | Penn |
| 4,386,077 | A | 5/1983 | Borgo |
| 4,704,361 | A | 11/1987 | Miccoli et al. |
| 4,764,603 | A | 8/1988 | Zappia et al. |
| 4,999,382 | A | 3/1991 | Wurtman et al. |
| 5,179,126 | A | 1/1993 | Wurtman et al. |
| 5,278,176 | A | 1/1994 | Lin |
| 5,409,946 | A | 4/1995 | Garvey et al. |
| 5,472,958 | A | 12/1995 | Gunn, Jr. et al. |
| 5,635,486 | A | 6/1997 | Yamamoto et al. |
| 5,691,320 | A | 11/1997 | von Borstel et al. |
| 5,691,365 | A | 11/1997 | Crooks et al. |
| 5,888,532 | A | 3/1999 | Pritsos et al. |
| 5,919,789 | A | 7/1999 | Dyke et al. |
| 5,958,896 | A | 9/1999 | Renshaw et al. |
| 5,977,174 | A | 11/1999 | Bradley et al. |
| 6,103,703 | A | 8/2000 | Renshaw et al. |
| 6,132,724 | A | 10/2000 | Blum |
| 6,153,653 | A | 11/2000 | Shashoua |
| 6,258,794 | B1 | 7/2001 | Renshaw |
| 6,277,855 | B1 | 8/2001 | Yerxa |
| 6,284,268 | B1 | 9/2001 | Mishra et al. |
| 6,319,953 | B1 | 11/2001 | Carlson et al. |
| 6,331,568 | B1 | 12/2001 | Horrobin |
| 6,410,522 | B1 | 6/2002 | Ruenberg |
| 6,503,951 | B2 | 1/2003 | Pischel et al. |
| 6,541,043 | B2 | 4/2003 | Lang |
| 6,608,064 | B2 | 8/2003 | McLean et al. |
| 6,624,195 | B2 | 9/2003 | Horrobin |
| 6,696,495 | B2 | 2/2004 | Mueller |
| 6,727,231 | B1 | 4/2004 | Page et al. |
| 6,852,870 | B2 | 2/2005 | Stoll |
| 6,989,376 | B2 * | 1/2006 | Watkins et al. ................. 514/50 |
| 7,026,301 | B2 | 4/2006 | Cardozo et al. |
| 7,053,064 | B2 | 5/2006 | Lukas |
| 2002/0019364 | A1 | 2/2002 | Renshaw |
| 2002/0028787 | A1 | 3/2002 | Watkins et al. |
| 2002/0182196 | A1 | 12/2002 | McCleary |
| 2003/0100844 | A1 | 5/2003 | Miller et al. |
| 2003/0114515 | A1 | 6/2003 | Wurtman et al. |
| 2003/0220291 | A1 | 11/2003 | Renshaw |
| 2003/0224435 | A1 | 12/2003 | Seiwert |
| 2003/0232827 | A1 | 12/2003 | Meltzer et al. |
| 2004/0167093 | A1 | 8/2004 | Lukas |
| 2004/0176316 | A1 | 9/2004 | Renshaw et al. |
| 2004/0192732 | A1 | 9/2004 | Pratt et al. |
| 2004/0266659 | A1 | 12/2004 | LaBerge |
| 2005/0113449 | A1 | 5/2005 | Renshaw |
| 2005/0129710 | A1 | 6/2005 | Renshaw et al. |
| 2006/0217344 | A1 | 9/2006 | Lukas |
| 2008/0132472 | A1 | 6/2008 | Renshaw |
| 2009/0054370 | A1 | 2/2009 | Renshaw |
| 2009/0215714 | A1 | 8/2009 | Renshaw et al. |

FOREIGN PATENT DOCUMENTS

| DE | 3400276 | 7/1985 |
|---|---|---|
| EP | 0 188 647 | 7/1986 |
| EP | 0 218 190 | 4/1987 |
| EP | 0 431 758 | 6/1991 |
| EP | 0 615 750 | 9/1994 |

(Continued)

OTHER PUBLICATIONS

Carlezon et al., "Antidepressant-like Effects of Uridine and Omega-3 Fatty Acids Are Potentiated by Combined Treatment in Rats," *Biol Psychiatry*, 2005, 57:343-350.

G.-Coviella et al., "Enhancement by Cytidine of Membrane Phospholipid Synthesis," *Journal of Neurochemistry*, 1992, 59:338-343.

(Continued)

*Primary Examiner*—Patrick T Lewis
(74) *Attorney, Agent, or Firm*—Clark & Elbing LLP

(57) ABSTRACT

The invention is based on the discovery that specific dosages of pyrimidine compositions, such as uridine compositions, can be used to treat patients diagnosed with bipolar disorder.

19 Claims, 8 Drawing Sheets

FOREIGN PATENT DOCUMENTS

| JP | 63-208524 | 8/1988 |
|---|---|---|
| JP | 08-183737 | 7/1996 |
| RU | 2003332 | 11/1993 |
| WO | WO 93/14076 | 7/1993 |
| WO | WO 99/26620 | 6/1999 |
| WO | WO 00/06174 | 2/2000 |
| WO | WO 00/11952 | 3/2000 |
| WO | WO 01/44265 | 6/2001 |
| WO | WO 01/72288 | 10/2001 |

OTHER PUBLICATIONS

Hansen, "Blood Nucleoside and Nucleotide Studies in Mental Disease," *The British Journal of Psychiatry*, 1972, 121:341-350.

Karkishchenko et al., "Biosynthesis of Endogenous Pyrimidines in Anxiety and Depressive States of Various Etiologies," *S.S. Korsakov Journal of Neuropathology and Psychiatry*, 1991, 91:73-74.

Repligen Press Release, "Repligen Reports Phase 1 Results of RG2133 in Bipolar Disorder and Depression Additional Studies Planned with Uridine in Biopolar Disorder," Jun. 9, 2004.

Repligen Press Release, "Repligen Reports Phase 1 Results of RG2133 in Bipolar Disorder and Depression Additional Studies Planned with Uridine in Biopolar Disorder," Jun. 10, 2004.

Repligen Press Release, "Repligen's RG2417 Demonstrates Positive Activity in Preclinical Model of Anxiety Data Presented at the Annual Meeting of the Society for Neuroscience," Oct. 25, 2004.

Repligen Press Release, "Repligen Reports Initial Clinical Data for Secretin in Schizophrenia," Feb. 4, 2005.

Stradomskii et al., "Pyrimidine Metabolism in Depression Anxiety Disorders," *Izvestiya Severo-Kavkazskogo Mauchnogo Tsentra Vysshei Shkoly Estestvennye Nauki*, 1990, 1:106-110.

van Groeningen et al., "Clinical and Pharmacologic Study of Orally Administered Uridine," *Journal of the National Cancer Institute*, 1991, 83:437-441.

van Groeningen et al., "Clinical and Pharmacokinetic Studies of Prolonged Administration of High-Dose Uridine Intended for Rescue from 5-FU Toxicity," *Cancer Treatment Reports*, 1986, 70:745-750.

Wurtman et al., "Effect of Oral CDP-Choline on Plasma Choline and Uridine Levels in Humans," *Biochemical Pharmacology*, 2000, 60:989-992.

Andreazza et al., "Oxidative Stress Markers in Bipolar Disorder: A Meta-Analysis," *J. Affect. Disord.* 111:135-144, 2008.

Agnoli et al., "Efficacy of CDPcholine in Chronic Cerebral Vascular Diseases (CCVD)," *Proceedings of the International Meeting on Novel Biochemical, Pharmacological and Clinical Aspects of Cytidinediphosphocholine*, Sorrento, Italy, Jun. 12-14, 1984, pp. 305-315.

Agut et al., "Cytidine(5')Diphosphocholine Enhances the Ability of Haloperidol to Increase Dopamine Metabolites in the Striatum of the Rat and to Diminish Stereotyped Behavior Induced by Apomorphine," *Neuropharmacology* 23:1403-1406, 1984.

Alvarez et al., "Double-Blind Placebo-Controlled Study with Citicoline in APOE Genotyped Alzheimer's Disease Patients. Effects on Cognitive Performance, Brain Bioelectrical Activity and Cerebral Perfusion," *Methods Find. Exp. Clin. Pharmacol.* 21:633-644, 1999. (Abstract).

Babb et al., "Differential Effect of CDP-Choline on Brain Cytosolic Choline Levels in Younger and Older Subjects as Measured by Proton Magnetic Resonance Spectroscopy," *Psychopharmacology* 127:88-94, 1996.

Biederman et al., "Non-Stimulant Treatments for ADHD," *Eur. Child Adolesc. Psychiatry* 9:151-159, 2000.

Boudouresques et al., "Therapeutic Conduct in Light of a Cerebral Vascular Accident and the Use of CDP-Choline," *International Symposium: Brain Suffering and Precursors of Phospholipids*, pp. 1-13, 1980.

Bronk et al., "The Transport and Metabolism of Naturally Occurring Pyrimidine Nucleosides by Isolated Rat Jejunum," *J. Physiol.* 395:349-361, 1988.

Brown et al., "CNS Complications of Cocaine Abuse: Prevalence, Pathophysiology, and Neuroradiology," *Am. J. Roentgenol.* 159:137-147, 1992.

Budney et al., "Marijuana Abstinence Effects in Marijuana Smokers Maintained in Their Home Environment," *Arch. Gen. Psychiatry* 58:917-924, 2001.

Carlezon et al., "Antidepressant-Like Effects of Cytidine in the Forced Swim Test in Rats," *Biol. Psychiatry* 51:882-889, 2002.

Castañé et al., "Lack of CB1 Cannabinoid Receptors Modifies Nicotine Behavioural Responses, But Not Nicotine Abstinence," *Neuropharmacology* 43:857-867, 2002.

Centrone et al., "Use of Citicoline in High Dosages in Acute Cerebrovascular Disease," *Minerva Med.* 77:371-373, 1986. English translation of Abstract.

Chang et al., "Neurochemical Alterations in Asymptomatic Abstinent Cocaine Users: A Proton Magnetic Resonance Spectroscopy Study," *Biol. Psychiatry* 42:1105-1114, 1997.

Christensen et al., "Abnormal Cerebral Metabolism in Polydrug Abusers During Early Withdrawal: A $^{31}$P MR Spectroscopy Study," *Magn. Reson. Med.* 35:658-663, 1996.

Cohen et al., "Decreased Brain Choline Uptake in Older Adults. An In Vivo Proton Magnetic Resonance Spectroscopy Study," *JAMA* 274:902-907, 1995.

Cohrs et al., "Sleep and Acetylcholine-Precursor-Substances," *Pharmacopsychiatry* 28:169, 1995. (Abstract).

Connolly et al., "Uridine and Its Nucleotides: Biological Actions, Therapeutic Potentials," *Trends Pharmacol. Sci.* 20:218-225, 1999.

Cyr et al., "Current Drug Therapy Recommendations for the Treatment of Attention Deficit Hyperactivity Disorder," *Drugs* 56:215-223, 1998.

English et al., "Elevated Frontal Lobe Cytosolic Choline Levels in Minimal or Mild AIDS Dementia Complex Patients: A Proton Magnetic Resonance Spectroscopy Study," *Biol. Psychiatry* 41:500-502, 1997.

Fernández, "Efficacy and Safety of Oral CDP-Choline: Drug Surveillance Study in 2817 Cases," *Arzneim.-Forsch.* 33:1073-1080, 1983.

Fioravanti et al., "Cytidinediphosphocholine (CDP-Choline) for Cognitive and Behavioural Disturbances Associated with Chronic Cerebral Disorders in the Elderly," *Cochrane Database Syst. Rev.* Apr. 18, 2005 (2):CD000269.

Fux et al., "A Placebo-Controlled Cross-Over Trial of Adjunctive EPA in OCD," *J. Psychiatr. Res.* 38:323-325, 2004.

G.-Coviella et al., "Effect of Cytidine(5')Diphosphocholine (CDP-Choline) on the Total Urinary Excretion of 3-Methoxy-4-Hydroxphenylglycol (MHPG) by Rats and Humans," *J. Neural Transm.* 66:129-134, 1986.

G.-Coviella et al., "Metabolism of Cytidine(5')-Diphosphocholine (CDP-Choline) Following Oral and Intravenous Administration to the Human and the Rat," *Neurochem. Int.* 11:293-297, 1987.

Gallai et al., "Study of the P300 and Cerebral Maps in Subjects With Multi-Infarct Dementia Treated With Cytidine," *Psychopharmacology* 103:1-5, 1991.

Galletti et al., "Biochemical Rationale for the Use of CDPcholine in Traumatic Brain Injury: Pharmacokinetics of the Orally Administered Drug," *J. Neural. Sci.* 103:S19-S25, 1991.

Geiger et al., "Cytidine and Uridine Requirement of the Brain," *J. Neurochem.* 1:93-100, 1956.

Giménez et al., "Changes in Brain Striatum Dopamine and Acetylcholine Receptors Induced by Chronic CDP-Choline Treatment of Aging Mice," *Br. J. Pharmacol.* 104:575-578, 1991.

Goodman and Gilman's, "The Pharmacological Basis of Therapeutics, 10$^{th}$ Ed.," *McGraw-Hill Medical Publishing Division*, pp. 54-57, 2001.

Grau et al., "Study on the Protection of CDP-Choline Against Nicotine Intoxication," *Arzneim.-Forsch.* 33:1025-1026, 1983.

Greenberg, "Clinical Dimensions of Fatigue," *Prim. Care Companion J. Clin. Psychiatry* 4:90-93, 2002.

Greenwell, "Enhancing Cognitive Function: Keeping Your Memory in Tip Top Shape," LE (Life Extension) Magazine, 2000. [Available at www.lef.org/magazine/mag2000/may00-cover-html.].

HD Blog, Health Care & Huntington's Disease News, "Triacetyluridine," downloaded from www.huntington.info, Dec. 3, 2003.
Hoff et al., "Effects of Crack Cocaine on Neurocognitive Function," Psychiatry Res. 60:167-176, 1996.
Interneuron Pharmaceuticals, Inc., "Citicoline Sodium (CDP-Choline), Investigator's Brochure," revised Apr. 1994.
Jacobs et al., "Cocaine Abuse: Neurovascular Complications," Radiology 170:223-227, 1989.
Jensen et al., "Triacetyluridine (TAU) Decreases Depressive Symptoms and Increases Brain pH in Bipolar Patients," Exp. Clin. Psychopharmacol. 16:199-206, 2008.
Jørgensen et al., "Herpes Simplex Virus (HSV) Antibodies in Child Psychiatric Patients and Normal Children," Acta Psychiatr. Scand. 66:42-49, 1982.
Katzung, "Basic & Clinical Pharmacolgy," Appleton & Lang, Seventh Edition, pp. 62 and 521-523, 1998.
Kaufman et al., "Cocaine-Induced Cerebral Vasoconstriction Detected in Humans With Magnetic Resonance Angiography," JAMA 279:376-380, 1998.
Kennedy et al., "The Function of Cytidine Coenzymes in the Biosynthesis of Phospholipides," J. Biol. Chem. 222:193-214, 1956.
Konradi et al., "Molecular Evidence for Mitrochondrial Dysfunction in Bipolar Disorder," Arch. Gen. Psychiatry 61:300-308, 2004. Correction reprinted in Arch. Gen. Psychiatry 61:538, 2004.
Koob et al., "Drug Addiction, Dysregulation of Reward, and Allostasis," Neuropsychopharmacology 24:97-129, 2001.
Kouri et al., "Changes in Aggressive Behavior During Withdrawal from Long-Term Marijuana Use," Psychopharmacology 143:302-308, 1999.
Kreek, "Opiate and Cocaine Addictions: Challenge for Pharmacotherapies," Pharmacol. Biochem. Behav. 57:551-569, 1997.
Levin et al., "Improved Regional Cerebral Blood Flow in Chronic Cocaine Polydrug Users Treated with Buprenorphine," J. Nucl. Med. 36:1211-1215, 1995.
London et al., "Cerebral Glucose Utilization in Human Heroin Addicts: Case Reports from a Positron Emission Tomographic Study," Res. Commun. Subst. Abuse 10:141-144, 1989.
Lukacsko et al., "Modulation of the Vasoconstrictor Response to Adrenergic Stimulation by Nucleosides and Nucleotides," J. Pharmocol. Exp. Ther. 222:344-349, 1982.
Lukas et al., "Effects of Short-Term Citicoline Treatment on Acute Cocaine Intoxication and Cardiovascular Effects," Psychopharmacology 157:163-167, 2001.
Lyoo et al., "Frontal Lobe Gray Matter Density Decreases in Bipolar I Disorder," Biol. Psychiatry 55:648-651, 2004.
Maas et al., "Functional Magnetic Resonance Imaging of Human Brain Activation During Cue-Induced Cocaine Craving," Am. J. Psychiatry 155:124-126, 1998.
Maldonado et al., "Involvement of the Endocannabinoid System in Drug Addiction," Trends Neurosci. 29:225-232, 2006.
Malec et al., "Influence of Adenosinergic Drugs on Ethanol Withdrawal Syndrome in Rats," Pot. J. Pharmacol. 48:583-588, 1996. (Abstract).
Martin et al. "Omega-3 Polyunsaturated Fatty Acids Increase Purine but Not Pyrimidine Transport in L1210 Leukaemia Cells," Biochem. J. 315:329-333 (1996).
Martinet et al., "Interaction of CDP-Choline with Synaptosomal Transport of Biogenic Amines and Their Precursors in Vitro and in Vivo in the Rat Corpus Striatum," Expetientia 34:1197-1199, 1978.
Martinet et al., "Effects of Cytidine-5'-Diphosphocholine on Norepinephrine, Dopamine and Serotonin Synthesis in Various Regions of the Rat Brain," Arch. Int. Pharmacodyn. 239:52-61, 1979.
McCance, "Overview of Potential Treatment Medications for Cocaine Dependence," NIDA Res. Monogr. 175:36-72, 1997.
Moglia et al., "Citicoline in Patients with Chronic Cerebrovascular Diseases (CCVD): Quantitative EEG Study," Curr. Ther. Res. 36:309-313, 1984.
Monti et al., "Adenosine Analogues Modulate the Incidence of Sleep Apnea in Rats," Pharmacol. Biochem. Behav. 51:125-131, 1995.

Monticone et al., "On the Therapeutic Use of Nucleosides, Cytidine and Uridine in Some, Neurological Diseases," Minerva Med. 57:4348-4352, 1966.
Moore et al., "Lower Levels of Nucleoside Triphosphate in the Basal Ganglia of Depressed Subjects: A Phosphorous-31 Magnetic Resonance Spectroscopy Study," Am. J. Psychiatry 154:116-118, 1997.
National Institutes of Health, "Problem Sleepiness," NIH Publication No. 97-4071, pp. 1-4, Bethesda, MD, 1997.
Naydenov et al., "Differences in Lymphocyte Electron Transport Gene Expression Levels Between Subjects with Bipolar Disorder and Normal Controls in Response to Glucose Deprivation Stress," Arch. Gen. Psychiatry 64:555-564, E1-E7, 2007.
Nicolson et al., "Evidence for Mycoplasma spp., Chlamydia pneunomiae, and Human Herpes Virus-6 Coinfections in the Blood of Patients with Autistic Spectrum Disorders," J. Neurosci. Res. 85:1143-1148, 2007.
O'Leary et al., "Acute Marijuana Effects on rCBF and Cognition: A Pet Study," NeuroReport 11:3835-3841, 2000.
O'Rourke et al., "Effect of Chronic Cocaine Exposure on Carotid Artery Reactivity in Neonatal Rabbits," Life Sci. 59:119-130, 1996.
Page et al. "Developmental Disorder Associated with Increased Cellular Nucleotidase Activity," Proc. Natl. Acad. Sci. U.S.A. 94:11601-11606, 1997.
Pekkanen, "Your Inner Clock," Washingtonian 42:131-134, 2007.
Peterson et al., "Neurovascular Complications of Cocaine Abuse," J. Neuropsychiatry Clin. Neurosci. 3:143-149, 1991.
Petkov et al., "Effects of the Nootropic Agents Adafenoxate, Meclofenoxate and the Acetylcholine Precursor Citicholine on the Brain Muscarinic Receptors (Experiments on Rats)," Acta Physiol. Pharmacol. Bulg. 13:3-10, 1987.
Petkov et al., "Changes in the Brain Biogenic Monoamines Induced by the Nootropic Drugs Adafenoxate and Meclofenoxate and by Citicholine (Experiments on Rats)," Gen. Pharmacol. 21:71-75, 1990.
Pleul et al., "Lithium Therapy and the Turnover of Phosphatidylcholine in Human Erythrocytes," Eur. J. Clin. Pharmacol. 31:457-462, 1986.
Purdue News, "Deficiency in Omega-3 Fatty Acids Tied to ADHD in Boys," Jun. 1996.
Radulovacki et al., "Adenosine Analogs and Sleep in Rats," J. Pharmacol, Exp, Ther. 228:268-274, 1984.
Regenold et al., "Cerebrospinal Fluid Evidence of Increased Extra-Mitrochondrial Glucose Metabolism Implicates Mitochondrial Dysfunction in Multlple Sclerosis Disease Progression," J. Neurol. Sci. 275:106-112, 2008.
Regenold et al., "Elevated Cerebrospinal Fluid Lactate Concentrations in Patients with Bipolar Disorder and Schizophrenia: Implications for the Mitochondrial Dysfunction Hypothesis," Biol. Psychiatry 65:489-494, 2009.
Rejdak et al., "Citicoline Treatment Increases Retinal Dopamine Content in Rabbits," Ophthalmic Res. 34:146-149, 2002.
Renshaw et al., "Short-Term Treatment with Citicoline (CDP-Choline) Attenuates Some Measures of Craving in Cocaine-Dependent Subjects: A Preliminary Report," Psychopharmacology 142:132-138, 1999.
Richardson et al., "Laterality Changes Accompanying Symptom Remission in Schizophrenia Following Treatment with Eicosapentaenoic Acid," Int. J. Psychophysiol. 34:333-339, 1999.
Saligaut et al., "Capture de Dopamine Striatale Chez le Rat: Effects d'une Hypoxie Hypobare Agüe et/ou d'un Traitement Oral Par la Cytidine Diphosphocholine" Circulation et Métabolisme du Cerveau 2:33-42, 1984.
Saligaut et al., "Circling Behaviour in Rats with Unilateral Lesions of the Nigrostriatum Induced by 6-Hydroxydopamine: Changes Induced by Oral Administration of Cytidine-5'-Diphosphocholine," Neuropharmacology 26:1315-1319, 1987.
Saligaut et al., "Effects of Hypoxia and Cytidine (5') Diphosphocholine on the Concentrations of Dopamine, Norepinephrine and Metabolites in Rat Hypothalamus and Striatum," Arch. Int. Pharmacodyn. Ther. 285:25-33, 1987.
Salvadorini et al., "Clinical Evaluation of CDP-Choline (NICHOLIN®): Efficacy as Antidepressant Treatment," Curr. Ther. Res. Clin. Exp. 18:513-520, 1975.

Satoh et al., "Involvement of Adenosine $A_{2A}$ Receptor in Sleep Promotion," *Eur. J. Pharmacol.* 351:155-162, 1998.

Scammell et al., "An Adenosine A2a Agonist Increases Sleep and Induces Fos in Ventrolateral Preoptic Neurons," *Neuroscience* 107:653-663, 2001.

Schloesser et al., "Cellular Plasticity Cascades in the Pathophysiology and Treatment of Bipolar Disorder," *Neuropsychopharmacology* 33:110-133, 2008.

Secades et al., "CDP-Choline: Pharmacological and Clinical Review," *Methods Find. Exp. Clin. Pharmacol.* 17(Suppl. B):1-54, 1995.

Self et al., "Opposite Modulation of Cocaine-Seeking Behavior by $D_1$- and $D_2$-Like Dopamine Receptor Agonists," *Science* 271:1586-1589, 1996.

Shargel et al., "Comprehensive Pharmacy Review," *Lippincott Williams & Wilkins, Fourth Edition*, pp. 547-548, 2001.

Shekim et al., "S-Adenosyl-L-Methionine (SAM) in Adults with ADHD, RS: Preliminary Results from an Open Trial," *Psychopharmacol. Bull.* 26:249-253, 1990.

Shibuya et al., "Effects of CDP-Choline on Striatal Dopamine Levels and Behavior in Rats," *Jpn. J. Pharmacol.* 31:47-52, 1981.

Sholar et al., "Concurrent Pharmacokinetic Analysis of Plasma Cocaine and Adrenocorticotropic Hormone in Men," *J. Clin. Endocrinol. Metab.* 83:966-968, 1998.

Spielman et al., "Treatment of Chronic Insomnia by Restriction of Time in Bed," *Sleep* 10:45-56, 1987.

Stoll et al., "Choline in the Treatment of Rapid-Cycling Bipolar Disorder: Clinical and Neurochemical Findings in Lithium-Treated Patients," *Biol. Psychiatry* 40:382-388, 1996.

Stork et al., "Mitochondrial Dysfunction in Bipolar Disorder: Evidence from Magnetic Resonance Spectroscopy Research," *Mol. Psychiatry* 10:900-919, 2005.

Sun et al. "Observation of Therapeutic Effects of High Dose Citicoline on the Emergency Treatment of 100 Cases of Hypnotics Poisoning," *China Pharmacist* 2:77-78, 1999. English translation (3 pages).

Tazaki et al., "Treatment of Acute Cerebral Infarction with a Choline Precursor in a Multicenter Double-Blind Placebo-Controlled Study," *Stroke* 19:211-216, 1988.

Teoh et al., "Acute Interactions of Buprenorphine with Intravenous Cocaine and Morphine: An Investigational New Drug Phase I Safety Evaluation," *J. Clin. Psychopharmacol.* 13:87-99, 1993.

Tornos et al., "Effect of Oral CDP-Choline on Experimental Withdrawal Syndrome," *Arzneim.-Forsch.* 33:1018-1021, 1983.

Tucker et al. "Inhibition by Adenosine Analogs of Opiate Withdrawal Effects," *NIDA Res. Monogr.* 49:85-91, 1984.

U.S. Surgeon General, "Overview of ADHD and its Treatments," *U.S. Office of the Surgeon General, Mental Health Matters*, pp. 1-6, 2000-2001.

Virtue, "Nutrition as Attention Deficit Disorder ADHD Alternative Treatment: Help is as Close as the Kitchen," downloaded from www.naturalhealthweb.com, 1999.

Warner et al., "Pharmacotherapy for Opioid and Cocaine Abuse," *Med. Clin. North Am.* 81:909-925, 1997.

Weiss, "Metabolism and Actions of CDP-Choline as an Endogenous Compound and Administered Exogenously as Citicoline," *Life Sci.* 56:637-660, 1995.

Wilson, "Increasing Serotonin Crucial for Treating Obsessive-Compulsive Disorder: Presented at SFN," *Doctor's Guide Personal Edition*, pp. 1-2, Nov. 14, 2003.

Wurtman et al., "Synaptic Proteins and Phospholipids are Increased in Gerbil Brain by Administering Uridine Plus Docosahexaenoic Acid Orally," *Brain Res.* 1088:83-92, 2006.

Wurtman et al., "Synapse Formation is Enhanced by Oral Administration of Uridine and DHA, the Circulating Precursors of Brain Phosphatides," *J. Nutr. Health Aging* 13:189-197, 2009.

Yoon et al., "Decreased Glutamate/Glutamine Levels May Mediate Cytidine's Efficacy in Treating Bipolar Depression: A Longitudinal Proton Magnetic Resonance Spectroscopy Study," *Neurophyschopharmacology* 34:1810-1818, 2009.

Zaharov et al., "Cognitive Disorders in Neurology Practice," A Difficult Patient No. 5, 2005. [Available at http://www.t-pacient.ru/archive/n5-2005/n5-2005_23.html].

Zhao et al., "Effects of Uridine in Models of Epileptogenesis and Seizures," *Epilepsy Res.* 70:73-82, 2006.

Zhao et al., "Effects of Uridine on Kindling," *Epilepsy Behav.* 13:47-51, 2008.

International Search Report and Written Opinion for PCT/US05/28407 (mailed Dec. 30, 2005).

* cited by examiner

PYRIMIDINES, SUCH AS URIDINE, IN TREATMENTS FOR PATIENTS WITH BIPOLAR DISORDER

CROSS REFERENCE TO RELATED APPLICATIONS

This application is a national phase application under 35 U.S.C. §371 of PCT International Application No. PCT/US2005/020690, filed on Jun. 10, 2005, which claims the benefit of priority, under 35 U.S.C. §119(e), from U.S. Provisional Patent Application Ser. No. 60/578,885, filed on Jun. 10, 2004. The contents of both of these applications are incorporated herein by reference in their entirety.

TECHNICAL FIELD

This invention relates to the treatment of bipolar disorder.

BACKGROUND

Bipolar disorder, which is also referred to as manic-depression, is a brain disorder that causes extreme shifts in a person's mood, thought, energy, behavior, and ability to function. The symptoms of bipolar disorder can be are severe, and can result in emotional problems, poor job or school performance, and even suicide. The name "bipolar" comes from the patients' mood swings, which can alternate between the "poles" of mania (highs) and depression (lows). These mood swings can be quite dramatic, from overly "high" and/or irritable to sad and hopeless, and then back again, often with periods of normal mood in between, and severe changes in energy and behavior go along with these changes in mood. Bipolar disorder typically develops in late adolescence or early adulthood. However, some people have their first symptoms during childhood or late in life. This disorder is not always viewed as an illness, and people may suffer for years before proper diagnosis.

Bipolar disorder has been separated into two categories, Type I and Type II, and is typically diagnosed following the guidelines in the Diagnostic and Statistical Manual of Mental Disorders (DSM) Fourth Edition, 1994 (American Psychiatric Association, 1400 K Street NW, Suite 1101, Washington, D.C. 20005-2403 USA). The fourth edition of these guidelines, DSM-IV, identifies the diagnostic features of Bipolar I Disorder as follows.

Bipolar I Disorder (DSM-IV, p. 350)

This disorder is a clinical course that is characterized by the occurrence of one or more Manic Episodes or Mixed Episodes. Often individuals have also had one or more Major Depressive Episodes. Episodes of Substance-Induced Mood Disorder (due to the direct effects of a medication, or other somatic treatments for depression, a drug of abuse, or toxin exposure) or of Mood Disorder Due to a General Medical Condition do not count toward a diagnosis of Bipolar I Disorder. In addition, the episodes are not better accounted for by Schizoaffective Disorder and are not superimposed on Schizophrenia, Schizophreniform Disorder, Delusional Disorder, or Psychotic Disorder Not Otherwise Specified.

The diagnostic features of Bipolar II Disorder are as follows.

Bipolar II Disorder (DSM-IV, p. 359)

This disorder is a clinical course that is characterized by the occurrence of one or more Major Depressive Episodes accompanied by at least one Hypomanic Episode. Hypomanic Episodes should not be confused with the several days of euthymia that may follow remission of a Major Depressive Episode. Episodes of Substance-Induced Mood Disorder (due to the direct effects of a medication, or other somatic treatments for depression, a drug of abuse, or toxin exposure) or of Mood Disorder Due to a General Medical Condition do not count toward a diagnosis of Bipolar I Disorder. In addition, the episodes are not better accounted for by Schizoaffective Disorder and are not superimposed on Schizophrenia, Schizophreniform Disorder, Delusional Disorder, or Psychotic Disorder Not Otherwise Specified.

The following diagnostic criteria, also from the DSM-IV apply.

Criteria for Major Depressive Episode (DSM-IV, p. 327)

A. Five (or more) of the following symptoms have been present during the same 2-week period and represent a change from previous functioning; at least one of the symptoms is either (1) depressed mood or (2) loss of interest or pleasure. Symptoms that are clearly due to a general medical condition, or mood-incongruent delusions or hallucinations should not be included.

Depressed mood most of the day, nearly every day, as indicated by either subjective report (e.g., feels sad or empty) or observation made by others (e.g., appears tearful). Note: In children and adolescents, can be irritable mood.

Markedly diminished interest or pleasure in all, or almost all, activities most of the day, nearly every day (as indicated by either subjective account or observation made by others)

Significant weight loss when not dieting or weight gain (e.g., a change of more than 5% of body weight in a month), or decrease or increase in appetite nearly every day. Note: In children, consider failure to make expected weight gains.

Insomnia or hypersomnia nearly every day.

Psychomotor agitation or retardation nearly every day (observable by others, not merely subjective feelings of restlessness or being slowed down).

Fatigue or loss of energy nearly every day.

Feelings of worthlessness or excessive or inappropriate guilt (which may be delusional) nearly every day (not merely self-reproach or guilt about being sick).

Diminished ability to think or concentrate, or indecisiveness, nearly every day (either by subjective account or as observed by others).

Recurrent thoughts of death (not just fear of dying), recurrent suicidal ideation without a specific plan, or a suicide attempt or a specific plan for committing suicide.

B. The symptoms do not meet criteria for a Mixed Episode.

C. The symptoms cause clinically significant distress or impairment in social, occupational, or other important areas of functioning.

D. The symptoms are not due to the direct physiological effects of a substance (e.g., a drug of abuse, a medication) or a general medical condition (e.g., hypothyroidism).

E. The symptoms are not better accounted for by bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

Criteria for Manic Episode (DSM-IV, p. 332)

A. A distinct period of abnormally and persistently elevated, expansive, or irritable mood, lasting at least 1 week (or any duration if hospitalization is necessary).

B. During the period of mood disturbance, three (or more) of the following symptoms have persisted (four if the mood is only irritable) and have been present to a significant degree:

Inflated self-esteem or grandiosity.

Decreased need for sleep (e.g., feels rested after only 3 hours of sleep).

More talkative than usual or pressure to keep talking.

Flight of ideas or subjective experience that thoughts are racing.

Distractibility (i.e., attention too easily drawn to unimportant or irrelevant external stimuli).

Increase in goal-directed activity (either socially, at work or school, or sexually) or psychomotor agitation.

Excessive involvement in pleasurable activities that have a high potential for painful consequences (e.g., engaging in unrestrained buying sprees, sexual indiscretions, or foolish business investments).

C. The symptoms do not meet criteria for a Mixed Episode.

D. The mood disturbance is sufficiently severe to cause marked impairment in occupational functioning or in usual social activities or relationships with others, or to necessitate hospitalization to prevent harm to self or others, or there are psychotic features.

E. The symptoms are not due to the direct physiological effects of a substance (e.g., a drug of abuse, a medication, or other treatments) or a general medical condition (e.g., hyperthyroidism).

Manic-like episodes that are clearly caused by somatic antidepressant treatment (e.g., medication, electroconvulsive therapy, light therapy) should not count toward a diagnosis of Bipolar I Disorder.

Criteria for Mixed Episode (DSM-IV, p. 335)

A. The criteria are met both for a Manic Episode and for a Major Depressive Episode (except for duration) nearly every day during at least a 1-week period.

B. The mood disturbance is sufficiently severe to cause marked impairment in occupational functioning or in usual social activities or relationships with others, or to necessitate hospitalization to prevent harm to self or others, or there are psychotic features.

C. The symptoms are not due to the direct physiological effects of a substance (e.g., a drug of abuse, a medication, or other treatment) or a general medical condition (e.g., hyperthyroidism).

Criteria for Hypomanic Episode (DSM-IV, p. 338)

A. A distinct period of persistently elevated, expansive, or irritable mood, lasting throughout at least 4 days, that is clearly different from the usual nondepressed mood.

B. During the period of mood disturbance, three (or more) of the following symptoms have persisted (four if the mood is only irritable) and have been present to a significant degree:

Inflated self-esteem or grandiosity.

Decreased need for sleep (e.g., feels rested after only 3 hours of sleep).

More-talkative than usual or pressure to keep talking.

Flight of ideas or subjective experience that thoughts are racing.

Distractibility (i.e., attention too easily drawn to unimportant or irrelevant external stimuli).

Increase in goal-directed activity (either socially, at work or school, or sexually) or psychomotor agitation.

Excessive involvement in pleasurable activities that have a high potential for painful consequences (e.g., engaging in unrestrained buying sprees, sexual indiscretions, or foolish business investments).

C. The episode is associated with an unequivocal change in functioning that is uncharacteristic of the person when not symptomatic.

D. The disturbance in mood and the change in functioning are observable by others.

E. The episode is not severe enough to cause marked impairment in social or occupational functioning, or to necessitate hospitalization, and there are no psychotic features.

F. The symptoms are not due to the direct physiological effects of a substance (e.g., a drug of abuse, a medication, or other treatment) or a general medical condition (e.g., hyperthyroidism).

Hypomanic-like episodes that are clearly caused by somatic antidepressant treatment (e.g., medication, electroconvulsive therapy, light therapy) should not count toward a diagnosis of Bipolar II Disorder.

Current drug therapy for bipolar disorder includes the use of lithium or valproic acid; however side effects are frequent and troublesome, and patients do not respond fully, leading to frequent recurrences of mania and depression.

SUMMARY

The invention is based, in part, on the discovery that individuals who are diagnosed with one or more symptoms of bipolar disorder can be treated with specific dosages of one or more pyrimidines, such as uridine. In particular, the invention is based on a phase I human clinical trial of a prodrug of uridine in patients with bipolar disorder.

Thus, in general, the invention features methods of treating an individual diagnosed as having one or more symptoms of bipolar disorder by administering to the individual an effective amount of a pyrimidine composition, such as a uridine composition. The individual may have one or more symptoms of bipolar disorder. For example, the amount of the uridine composition can be effective to improve one or more of the symptoms of bipolar disorder. For example, the effective amount of the uridine composition can provide about 0.1 to 10 grams/day, e.g., about 0.25, 0.5, 0.75, 1, 2, 3, 4, or 5 grams/day, or 1 to 250 mg, e.g., 10 to 50 mg, of uridine/kg of body weight/day. The uridine composition can be administered orally, for example, when the uridine composition includes uridine and a liquid ingestible carrier. In specific embodiments, the uridine composition can be acylated derivatives of uridine, such as triacetyl uridine.

A pyrimidine composition is either a purified pyrimidine, a compound or product that contains a pyrimidine, a compound that increases the level of a pyrimidine in the patient, or a compound or molecule that mimics the biological function of a pyrimidine. Such a compound can be a pyrimidine precursor or prodrug, which is processed, e.g., metabolized, degraded, or cleaved, in the body to form a pyrimidine. Such a compound can also be a pyrimidine derivative, which includes pyrimidine, and other molecules or compounds bound (e.g., covalently or non-covalently) to a pyrimidine, but that do not impair the pyrimidine's biological activity in patients with increased purine levels. Such compounds can also be pyrimidine mimetics, such as other nucleotides or small molecules that have a sufficiently similar three-dimensional shape or electron configuration that the compound has at least 50 percent of the biological activity of the pyrimidine. Such compounds can also be drugs or other compounds that induce the body to produce one or more pyrimidines.

For example, a pyrimidine composition can be a uridine composition. A uridine composition is either a purified uridine, a compound or product that contains uridine, a compound that increases the level of uridine in the patient, or a compound or molecule that mimics the biological function of uridine. Such a compound can be a uridine precursor or prodrug, which is processed, e.g., metabolized, degraded, or cleaved, in the body to form uridine. Such a compound can also be a uridine derivative, which includes uridine, and other molecules or compounds bound (e.g., covalently or non-covalently) to uridine, but that do not impair uridine's biological activity in patients with increased purine levels. Such compounds can also be uridine mimetics, such as other nucleotides or small molecules that have a sufficiently similar three-dimensional shape or electron configuration that the compound has at least 50 percent of the biological activity of uridine. Such compounds can also be drugs or other compounds that induce the body to produce uridine.

In one aspect, the invention includes a method of treating an individual exhibiting one or more symptoms of bipolar disorder (e.g., type I or type II bipolar disorder) by administering to the individual an effective amount of a uridine composition. Uridine compositions can include triacetyl uridine, and/or other uridine precursors or mimetics, e.g., UTP, UDP, or UMP. An effective amount of the uridine composition can be an amount sufficient to improve one or more symptoms of bipolar disorder, e.g., one or more symptoms of a major depressive episode, one or more symptoms of a manic episode, one or more symptoms of a mixed episode, or one or more symptoms of a hypomanic episode.

In another aspect, the invention includes a method of reducing anxiety in an individual suffering from bipolar disorder by administering to the individual an effective amount of a uridine composition. In another aspect the invention includes a method of reducing the severity of manic symptoms in an individual in need of treatment for bipolar disorder by administering to the individual an effective amount of a uridine composition.

By "treating" is meant the medical management of a patient to cure, ameliorate, or prevent a specific disorder. This term includes active treatment directed towards improvement of a disorder, and causal treatment directed towards the removal of a cause of the disorder. In addition, this term includes palliative treatment designed for the relief of one or more symptoms rather than curing the disorder; preventive treatment directed to prevention of the disorder; and supportive treatment employed to supplement another specific therapy directed toward the improvement of the disorder.

By "therapeutically-effective amount" is meant an amount of a uridine composition sufficient to produce a healing, curative, prophylactic, stabilizing, or ameliorative effect in the treatment of bipolar disorder. Such an effect is sufficient even if it improves only one symptom in a patient.

The new methods provide a safe therapy for bipolar disorder, without the side effect of mania, which can accompany other known treatments.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

DETAILED DESCRIPTION

Figure 1:
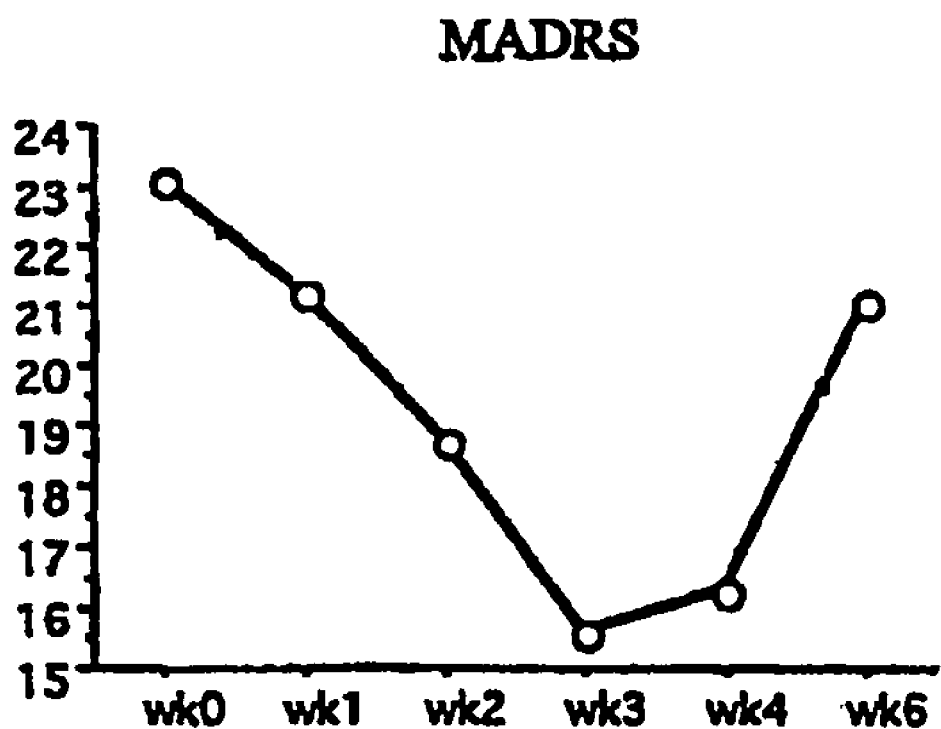
FIG. 1 is a graph showing the weekly Montgomery-Asberg Depression (MADRS) scores of patients treated with uridine.

The new methods are based on the finding that individuals diagnosed with bipolar disorder can benefit from treatment by the administration of specific dosages of one or more pyrimidines, such as uridine, prodrugs of uridine, and uridine analogs. The patient can be easily treated by the administration of an effective amount of a pyrimidine composition such as a uridine composition, for example, by oral or systemic intravenous administration.

The new methods are based on a Phase I open-label clinical trial of RG2133, a prodrug of uridine, designed to assess the impact of uridine in patients with bipolar disorder. The results demonstrate that administration of RG2133 in this patient population was safe, did not induce mania, a potential and concerning side effect of existing therapy, and provides evidence of a clinical effect of the drug. The trial assessed the impact of daily, oral administration of escalating doses of RG2133 over a 6 week period on the symptoms associated with bipolar disorder, which are not adequately treated with existing drugs including SSRIs such as Prozac® or Zoloft®. The trial included 11 patients.

General Methods of Therapy

The new methods involve the administration of an effective amount of a pyrimidine composition, such as a uridine composition, to a patient diagnosed with one or more symptoms of bipolar disorder. The uridine composition can be formulated into a therapeutic composition and administered using a variety of known routes of administration, and in various dosage forms.

To formulate pharmaceutical grade therapeutic compositions, the uridine composition can be purified by standard methods, e.g., filtration, to remove contaminants, if present. The final compositions can be lyophilized and resuspended in sterile, deionized water before further compounding. The therapeutic compositions can be formulated as solutions, suspensions, suppositories, tablets, granules, powders, capsules, ointments, or creams. In the preparation of these compositions, at least one pharmaceutical excipient can be included. Examples of pharmaceutical excipients include solvents (e.g., water or physiological saline), solubilizing agents (e.g., polysorbates, or Cremophor EL7), agents for achieving isotonicity, preservatives, antioxidizing agents, lactose, crystalline cellulose, mannitol, maltose, calcium hydrogen phosphate, light silicic acid anhydride, calcium carbonate, binders (e.g., starch, polyvinylpyrrolidone, hydroxypropyl cellulose, ethyl cellulose, carboxy methyl cellulose, or gum arabic), lubricants (e.g., magnesium stearate, talc, or hardened oils), or stabilizers (e.g., lactose, mannitol, maltose, polysorbates, macrogols, or polyoxyethylene hardened castor oils). If desired, glycerin, dimethylacetamide, 70% sodium lactate, surfactant, or basic substances such as sodium hydroxide, ethylenediamine, ethanolamine, sodium bicarbonate, arginine, meglumine, or trisaminomethane can be added. Common disintegrants that can be included in the composition include croscarmellose sodium, crospovidone, gellan gum, and sodium starch glycolate.

When the pyrimidine composition, e.g., a uridine composition, is ingested, the excipient or carrier can be water, a flavored beverage such as a fruit juice, broth, carbonated beverage, milk, or milk shake.

Biodegradable polymers such as poly-D,L-lactide-co-glycolide or polyglycolide can be used as a bulk matrix if slow release of the composition is desired (see, e.g., U.S. Pat. Nos. 5,417,986, 4,675,381, and 4,450,150). Pharmaceutical preparations such as solutions, tablets, granules or capsules can be formed with these components. If the composition is to be administered orally, flavorings and/or colors can be added.

The new compositions can be administered via any appropriate route, e.g., intravenously, intraarterially, topically, transdermally, by injection, intraperitoneally, intrapleurally, orally, subcutaneously, intramuscularly, sublingually, nasally, by inhalation, intraepidermally, or rectally, using standard techniques.

Dosages administered in practicing the new methods will depend on factors including the specific uridine composition used and its concentration in the composition, the mode and frequency of administration, the age, weight, sex, and general health of the subject, and the severity of the autistic symptoms. In general, the new compositions can be administered in amounts ranging between 1.0 mg and 200 mg of uridine per kilogram of body weight per day, e.g., 2, 3, 5, 10, 20, 50, or 100 mg/kg/day.

A general dosage is between 3 and 100 mg/kg/day, e.g., which can be 0.25 to 7 grams (e.g., 0.25, 0.5, or 1 grams) per patient per day. Oral tablets of triacetyl uridine can be used. The daily dosage is administered on an ongoing basis until symptoms subside.

Dosages can be administered with meals or once, twice, or more times per day to achieve the best relief of symptoms. The dosage should be adjusted to provide a reduction in symptoms. Once the proper dosage is determined, it can be easily maintained over time as required. In general, 5 to 15 µM is the normal plasma concentration of uridine with a volume distribution around 0.634 liters/kg. Following administration of a uridine composition, e.g., triacetyl uridine, blood plasma levels of about 50 to 300 µM are in the therapeutic range. Clinical results also indicate that overly high doses are not effective.

Administration is repeated as necessary, as determined by one skilled in the art. By varying the amount of the composition or dosage, the administration protocol can be optimized based on the present disclosure to elicit a maximal improvement in symptoms of bipolar disorder. Physicians, pharmacologists, and other skilled artisans are able to determine the most therapeutically effective treatment regimen, which will vary from patient to patient. The potency of a specific composition and its duration of action can require administration on an infrequent basis, including administration in an implant made from a polymer that allows slow release of the uridine.

Skilled artisans are also aware that the treatment regimen must be commensurate with issues of safety and possible toxic effect produced by the uridine or other components in the compositions. Thus, before administering the above compositions to humans, toxicity testing can be conducted in animals, e.g., as described in Examples below. In an example of toxicity testing, the uridine compositions can be administered to mice via an oral or parenteral route with varying dosages of uridine in the composition, and the mice observed for signs of toxicity using standard techniques. Of course, if the uridine composition is pure uridine, long-term experience has shown that uridine has no known toxic effects at dosages of up to 1000 mg/kg/day. Higher dosages may cause mild diarrhea in some patients. See, e.g., Leyva et al., Cancer Res., 4:5928-5933 (1984) (high dose uridine used to rescue patients from 5-fluorouracil toxicity) and Webster et al., Chapter 55, pages 1799-1837, in "The Metabolic and Molecular Bases of Inherited Disease," 7th Ed., Scriver et al. (eds.) (McGraw-Hill, Inc., New York, N.Y., 1995) (treatment of orotic aciduria with uridine, see, e.g., page 1815).

Uridine Compositions

A uridine composition is either purified uridine, a compound or product that contains uridine, a compound that increases the level of uridine in the patient, or a compound or molecule that mimics the biological function of uridine. Such a compound can be a uridine precursor or prodrug, which is processed, e.g., metabolized, degraded, or cleaved, in the body to form uridine. Such a compound can also be a uridine derivative, which includes uridine, and other molecules or compounds bound (e.g., covalently or non-covalently) to uridine, but that do not impair uridine's biological activity in patients with increased purine levels. Such compounds can also be uridine mimetics, such as other nucleotides or small molecules that have a sufficiently similar three-dimensional shape or electron configuration that the compound has at least 50 percent of the biological activity of uridine. Such compounds can also be drugs or other compounds that induce the body to produce uridine, or drugs or compounds that inhibit degradation or otherwise prolong the half-life of uridine in the body.

Uridine precursors or prodrugs include orotic acid, mono-, di- or tri-esters of uridine, including mono-, di-, and triacetyl uridine, and mono, di- or tri-phosphates of uridine including uridine monophosphate (UMP) uridine diphosphate (UDP) and uridine triphosphate (UTP). Uridine mimetics include cytidine and mono-, di-, or tri-phosphates of cytidine including cytidine monophosphate, as well as mono-, di-, or tri-esters of cytidine including triacetyl cytidine. Deoxy-versions of these and other ribonucleosides may also be useful.

Uridine compositions also include encapsulated uridine, e.g., liposome- or polymer-encapsulated uridine. Uridine compositions also include uridine linked (e.g., covalently or non-covalently) to various antibodies, ligands, or other targeting and enveloping or shielding agents (e.g., albumin or dextrose), to allow the uridine to reach the target site (e.g., the central nervous system, muscle cells, or the peripheral nervous system) prior to being removed from the blood stream, e.g., by the kidneys and liver, and prior to being degraded.

Uridine salts or food products containing uridine that transform into uridine upon administration to a host such as human can also be used.

Useful uridine-containing compounds include, without limitation, any compound comprising uridine, UTP, UDP, or UMP. Uridine and uridine-containing compounds and analogs are well tolerated in humans. For example, triacetyl uridine (TAU) is a prodrug for the naturally occurring compound uridine. Enteral dosages of TAU are rapidly metabolized to uridine and uracil and these metabolites are the compounds observed in blood, not the prodrug. Elevation of uridine blood levels to reverse toxicity of Fluorouracil in cancer patients has been tested using intravenous (van Groeningen et al., 1986, Cancer Treat. Rep., 70:745-750) or oral (van Groeningen et al., 1991, J. Natl. Cancer Inst., 83(6): 437-441) dosing with uridine. Studies of uridine infusion achieved plasma concentrations >100 fold above baseline values (3 µM) with fever as the observed side effect. Oral dosing of uridine in 6 healthy volunteers and 9 cancer patients showed a maximum tolerated dose without side effects of 10 g/m$^2$ for a single dose and 5 g/m$^2$ for multiple dosing every 6 hours. Bioavailability of uridine was 5.8-9.9% and peak plasma levels of 80 µM uridine. No toxicity was observed at doses of 8 g/m$^2$ or less. At 10 or 12 g/m$^2$ cramps and diarrhea were reported. Repeat doses every 6 hours of 8 g/m$^2$ resulted in diarrhea.

TAU has also been used in preliminary clinical studies of oral dosing to treat fluorouracil toxicity (Kelsen et al., 1997, J. Clin. Oncol., Apr. 15(4):1511-1517). Both suspension and tablet forms of TAU were given at 6 g/dose every 6 hours for 9 doses that achieved peak blood uridine levels of 167 µM. Diarrhea was seen in cancer patients receiving TAU but overlying cancer and fluorouracil toxicities made drug toxicity evaluation equivocal. A reduction in hematologic toxicities associated with fluorouracil was observed in patients receiving TAU at this dose. The first dose level used in this study, 6 g/day or 2 g/dose, was expected to achieve a maximum uridine blood level about 10 fold over baseline values, which is between 5 and 50 µM. Preliminary results from patient studies (see Example 3) suggest that lower doses of uridine may also be therapeutically effective, and that too high a dose of uridine may reduce the therapeutic effect.

Combination with Other Therapeutics

The pyrimidine, e.g., uridine, compositions described herein can be administered as a monotherapy, as combinations of two or more different pyrimidines, e.g., uridine compositions (or uridine and cytidine compositions), or in combination with other compounds for the treatment of bipolar disorders.

For example, the pyrimidine compositions can be administered in conjunction with lower doses of current treatments for bipolar disorder, including stimulants and antidepressants. For example, divalproex sodium (DEPAKOTE®) has been used to treat bipolar disorder.

In particular examples, the pyrimidine compositions may be administered in combination with an antidepressant, anticonvulsant, antianxiety, antimanic, antipyschotic, antiobsessional, sedative, stimulant, or anti-hypertensive medication. Examples of these medications include, serotonin reuptake inhibitors, monoamine oxidase inhibitors, tricyclic antidepressants, dopamine agonists (e.g., bromocriptine, pergolide), bupropion, venlafaxine, nefazodone, benzodiazepine, trazodone, lithium (Li), risperidone, topiramate, lamotrigine, gabapentin, nimodipine, divalproex, quetiapine, divalproex, lamotrigine, carbamazepine, clozapine, olanzapine, topiramate, thyroid hormone (e.g., T3 or T4), Omega-3 fatty acids, calcium channel blockers (other than nimodipine), tiagabine, cholinesterase inhibitors, tamoxifen, and phenytoin.

EXAMPLES

The invention is further described in the following examples, which do not limit the scope of the invention described in the claims.

Example 1

Triacetyl Uridine RG2133

The investigational drug used in the Examples below was RG2133 (2',3',5'-tri-O-acetyluridine). RG2133 was produced under cGMP conditions from uridine via exhaustive acetylation and purified by repeated precipitation after residual acetic anhydride is removed by distillation. The purified drug substance was dried under reduced pressure and sieved to obtain a uniform solid.

Example 2

Toxicology Studies in Rodents

RG2133 has been tested in a repeat dose rodent toxicity and toxicokinetic study. Three groups of ten male and ten female rats (Crl: CD® (SD)IGS BR strain) received RG2133 orally, by gavage, at dosages of 300, 1000, or 2000 mg/kg/day (administered as 150, 500, or 1000 mg/kg b.i.d.) in aqueous 1% carboxymethylcellulose with methyl paraben (at 1.8 g/l) and propyl paraben (at 0.2 g/l) for four weeks. Animals were examined by observation and lab analysis of blood and urine for evidence of toxicity, and results are shown in Table 1. Tissues were examined microscopically for evidence of drug related toxicity. The repeated oral administration of RG2133 at dosages up to 2000 mg/kg/day (administered as 1000 mg/kg b.i.d.) for 28 days was well tolerated and produced no toxicologically significant changes. The no-observed-adverse-effect-level (NOAEL) was considered to be 2000 mg/kg/day (1000 mg/kg b.i.d.).

TABLE 1

Rat Plasma Uridine Following Oral Gavage of TAU Suspension, RG2133

| Dose (g/kg/day) | $C_{max}$ (µM) | Fold Change ($C_{max}/C_o$) | $T_{max}$ (hr) | $AUC_{0-24h}$ (µmol hr/L) | $T_{1/2}$ (hr) |
|---|---|---|---|---|---|
| 0.3 | 18.2 ± 1.9 | 6.1 ± .07 | 0.39 ± 0.04 | 93.3 ± 6.8 | 4.14 ± 1.20 |
| 1.0 | 104 ± 18.3 | 35.8 ± 7.5 | 0.42 ± 0.04 | 147.8 ± 7.0 | 1.28 ± 0.08 |
| 2.0 | 182 ± 25.6 | 60.1 ± 10.4 | 0.54 ± 0.05 | 225.2 ± 17.4 | 0.97 ± 0.12 |

$C_o$, baseline plasma uridine value is 3 µM.

Toxicokinetic studies performed in a satellite group of animals provided information on the bioavailability, peak plasma levels of uridine and elimination rates. Bioavailability was ~40% for each dose tested.

Pharmacological activity of RG2133 was observed in rodents during repeat dose toxicology study. The procedure of oral gavage was shown to increase blood lactate levels in rats presumably as a stress response to the procedure. Plasma lactate levels showed peak elevations of 3-6 fold from 10 minutes to 4 hours post dosing. RG2133 showed a dose dependent decrease in the $C_{max}$ and AUC of lactate elevation. RG2133 did not reduce the lactate level below the normal baseline value (2.4 mM). This result is consistent with reports of anxiolytic and anticonvulsant activity of uridine and a postulated biological function as a GABAa receptor agonist (Guarneri et al., 1985, November-December; 26(6):666-71).

Example 3

Patient Studies

Outpatients with bipolar disorder were recruited for this 6-week open-label study. Patients' daily dose amounts were divided into three daily doses. Subjects received an initial RG2133 dose of 6 g/day. During the course of the study subjects who responded favorably, maintained the initial dose. Patients who did not respond favorably received increasing doses during the third week, ending with a dose of about 12 g/day (mean dose 11.17 g/day). For patients that did not respond favorably to 12 g/day, the dose was increased to about 18 g/day. Subjects were monitored for changes in mood using standard rating scales. The subjects' physical status was followed clinically and with standard laboratory measures to monitor for any adverse effects and/or toxicity.

During the baseline visit, a detailed psychiatric and medical history was obtained, and the following standard rating scales were performed: Structured Clinical Interview for DSM-IV (SCID) for diagnosis, Young Mania Rating Scale (YMRS), Montgomery-Asberg Depression rating Scale (MADRS), the Hamilton Anxiety Scale (HAMA), Clinical Global Impression scale (CGI), the Global Assessment of Function (GAF) scale, quality of life scale (SF-36), as well as a brief adverse-effect rating scale.

After the baseline evaluation, patients returned for office visits at weeks 1, 2, 3, 4, and 6. The same rating scales were performed at each follow-up office visit, except for the SCID. Instead of the full SCID at the follow-up visits, only the SCID screening questions for mania and depression were performed to aid in the determination of syndromic recovery or recurrence. In addition, patients maintained a daily Mood Diary, which was reviewed at each study visit to elicit symptom recall. Routine clinical and laboratory evaluations of each patient's physical status occurred at baseline and at regular intervals. Subjects were monitored for changes in mood using standard rating scales. The subjects' physical status was followed clinically and with standard laboratory measures to monitor for any adverse effects and/or toxicity.

Criteria for Inclusion in the Study:
1) Patients with bipolar disorder (type I or II)
2) Patients must have had subsyndromal or syndromal symptoms or mania, hypomania, mixed mania, or depression.
3) Patients include both male and female; ages 21-65.
4) If a subject was receiving ongoing pharmacotherapy, no dosage changes occurred in the 2 weeks prior to the study.
5) No new pharmacological or psychotherapeutic treatments were introduced within the 4 weeks prior to the study.

Criteria for Exclusion from the Study:
1) Patients enrolled in another clinical research trial or receiving another experimental drug within 30 days prior to initiation of this study.
2) Patients with active medical or neurological disorders.
3) Patients, who in the Principal Investigator's judgment have active suicidal or homicidal ideation.
4) Patients, who in the Principal Investigator's judgment would be unable to comply with the study protocol.
5) Significant psychiatric comorbidity.
6) Patients whose baseline laboratories indicate abnormal hepatic function (AST, ALT or bilirubin >1.25 times the upper limit of normal), abnormal renal function (BUN or creatinine >1.25 times the upper limit of normal), or abnormal bone marrow function (WBC <4×10$^3$/cubic mm, platelets <100×10$^3$/cubic mm and hemoglobin <10 g/dl).

Individual Patient Histories

Patient #3 was a 36-year-old male suffering from bipolar II disorder, taking antidepressant medication. He received an initial RG2133 dose of 6 g/day. After one week of treatment, his dose was gradually increased to 12 g/day by the end of the second week of treatment. After three weeks of treatment, his medication was gradually decreased to 6 g/day, by the end of the fourth week; and his dose was maintained at 6 g/day until completion of the study after six weeks. The patient exhibited slight hypomania at week three, which led to the decision to lower his dose to 6 g/day.

Patient #4 was 29-year-old female suffering from bipolar I disorder, taking antidepressant medication. She received an initial RG2133 dose of 6 g/day. After one week of treatment, her dose was gradually increased to 12 g/day by the end of the second week of treatment. Her dose was held constant at 12 g/day until completion of the study at week six. The patient reported that, although the study was occurring during the most difficult time of the year for her, she was feeling stable. She exhibited some hypomania at week three, and her mood deteriorated at week six.

Patient #5 was a 53-year-old female suffering from bipolar I disorder, taking no antidepressant medication. She received an initial RG2133 dose of 6 g/day, which was held constant through the first two weeks of the study. After the second week, her dose was gradually increased to 7.5 g/day by the end of the third week. After the fourth week, her dose was gradually increased to 9 g/day. Her dose was held at 9 g/day from week four until completion of the study at week six. The patient reported a significant change in mood at week one, saying she felt better than she had felt in a long time.

Patient #6 was a 46-year-old female suffering unspecified form of bipolar disorder, taking no antidepressant medication. She received an initial RG2133 dose of 6 g/day, which was held constant until completion of the study at the end of week six. One day during the last week of the study the patient reported taking 12 g/day because she wanted to see if the dose change would alter her mood. The patient reported some eye pain similar to when she had previously taken Topomax. The patient also reported feeling significantly better than she had in two years.

Patient #7 was a 44-year-old male suffering bipolar I disorder, taking antidepressant medication. He received an initial RG2133 dose of 6 g/day. After one week of treatment, his dose was gradually increased to 12 g/day by the end of the second week of treatment. After the third week of treatment, his medication was gradually increased to 18 g/day by the end of week four. The patient's dose was maintained at 18 g/day until completion of the study after week six. The patient reported no change in mood.

Patient #11 was a 46-year-old female suffering bipolar II disorder, taking antidepressant medication. She received an initial RG2133 dose of 6 g/day. After one week, her dose was gradually increased to 12 g/day by the end of the second week of treatment. Her dose was held constant at 12 g/day until completion of the study after week six. The patient had a severe bout of colitis. The patient underwent a complete remission at week four in her bipolar symptoms.

Patient #13 was a 42-year-old male suffering bipolar I disorder, taking no antidepressant medication. He received an initial RG2133 dose of 6 g/day, which was held constant until week three of the study. Between weeks three and four, his medication was gradually increased to 9 g/day, and maintained at 9 g/day until completion of the study at six weeks. The patient reported feeling less depressed and more hopeful. He experienced a slight change in depth perception leading to two falls.

Patient #15 was female suffering bipolar II disorder, taking no antidepressant medication. She received an initial RG2133 dose of 6 g/day. After one week, her dose was gradually increased to 12 g/day by the end of the second week of treatment. She reported feeling less volatile and fewer mood swings on RG2133. After three weeks of treatment, the patient reduced her medication back to 6 g/day in response to complaints of dizziness spells, constipation, and a reported manic episode. This patient was terminated from the study during the third week because of noncompliance and impending shoulder surgery.

Patient #16 was a 41-year-old male suffering bipolar II disorder, taking antidepressant medication. He received an initial RG2133 dose of 6 g/day. After the first week of the study, his medication was gradually increased to 12 g/day by the end of the second week. This dose was held constant through the third week of the study. The patient reported no change in mood and complained of loose stools and increased flatulence.

Patient #17 was a 56-year-old male suffering bipolar II disorder, taking antidepressant medication. He received an initial RG2133 dose of 6 g/day. After the first week of the study, his medication was gradually increased to 12 g/day by the end of the second week. This dose was held constant through the third week of the study. The patient reported no change in mood and complained of loose stools and increased flatulence.

Patient #18 was a 67-year-old male suffering bipolar II disorder, taking no antidepressant medication. He received an initial RG2133 dose of 6 g/day. After the first week of the study, his medication was gradually increased to 12 g/day by the end of the second week. After the third week of the study, the patient's dose was gradually reduced to 6 g/day by the end of the fourth week. The 6 g/day dose was held constant for the remaining two weeks of the study.

Patient #19 was female suffering an unspecified form of bipolar disorder. She received an initial RG2133 dose of 6 g/day. After the first week of the study, her medication was gradually increased to 12 g/day by the end of the second week. After the third week of the study, the patient's dose was gradually increased to 18 g/day by the end of the fourth week. The 18 g/day dose was held constant for the remaining two weeks of the study.

Cumulative Results of Patient Studies

Example 3A

MADRS

During the study patients were evaluated using the Montgomery-Asberg Depression Rating Scale (MADRS). This scale measures the effect of treatment on depression severity relative to a baseline assessment before treatment. The MADRS measures the severity of a number of symptoms on a scale from 0 to 60, including mood and sadness, tension, sleep, appetite, energy, concentration, suicidal ideation, and restlessness. Increasing scores reflect a greater severity of depression. Scores of 15-25 on the MADRS scale indicate moderate depression. Scores above 25 indicate clinically severe depression.

As shown in FIG. 1, bipolar patients exhibited a slight decrease in average MADRS scores during the first three weeks of treatment. MADRS scores then rose slightly between week three and week six. Averaged MADRS scores never returned to baseline levels or above. The data indicate that generally, study patients were not severely depressed at the outset of the study, and the administration of RG2133 did not significantly worsen patients' depression, and may have slightly improved patients' depression, especially during the first half of the study, during which lower doses were administered than in the second half for those subjects responding to RG2133.

Example 3B

YMRS

During the study patients were also evaluated using the Young Mania Rating Scale (YMRS). This scale assesses the severity of mania in patients already diagnosed with mania based on a personal interview. Scores of 1 to 12 are not considered to be suffering from mania, whereas a score of 13 indicates minimal mania. Increasing scores to 44, indicate progressively severe mania.

Figure 2:
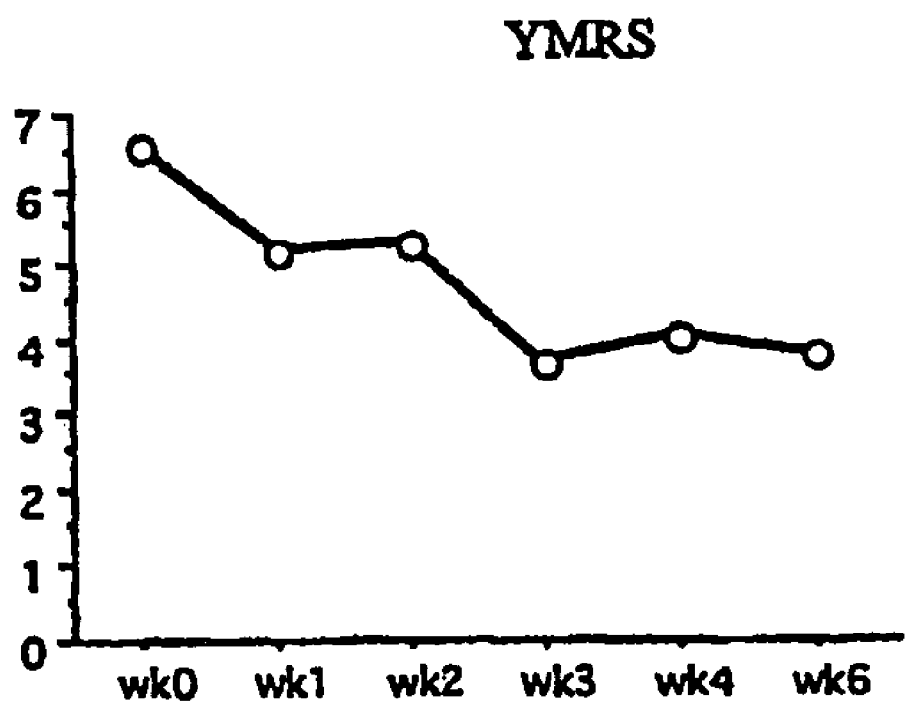
FIG. 2 is a graph showing the weekly Young Mania Rating Scale (YMRS) scores of patients treated with uridine.

As shown in FIG. 2, bipolar patients exhibited a slight decrease in averaged YMRS scores during the course of the study. This result is significant because many drugs that have been used to treat bipolar disorder in the past have induced mania in patients.

Example 3C

CGI

During the study patients were also evaluated using Clinical Global Impression (CGI) scale. A clinician rated the severity of the patient's illness relative to the clinician's past experience with patients with the same diagnosis. At the outset of the study a clinician created a baseline single item score on a 7 point scale from 1 ('normal', not ill) to 7 (extremely ill). CGI was then used to track the clinical distance between a patient's individual's current condition and his or her baseline condition at the start of treatment.

Figure 3:
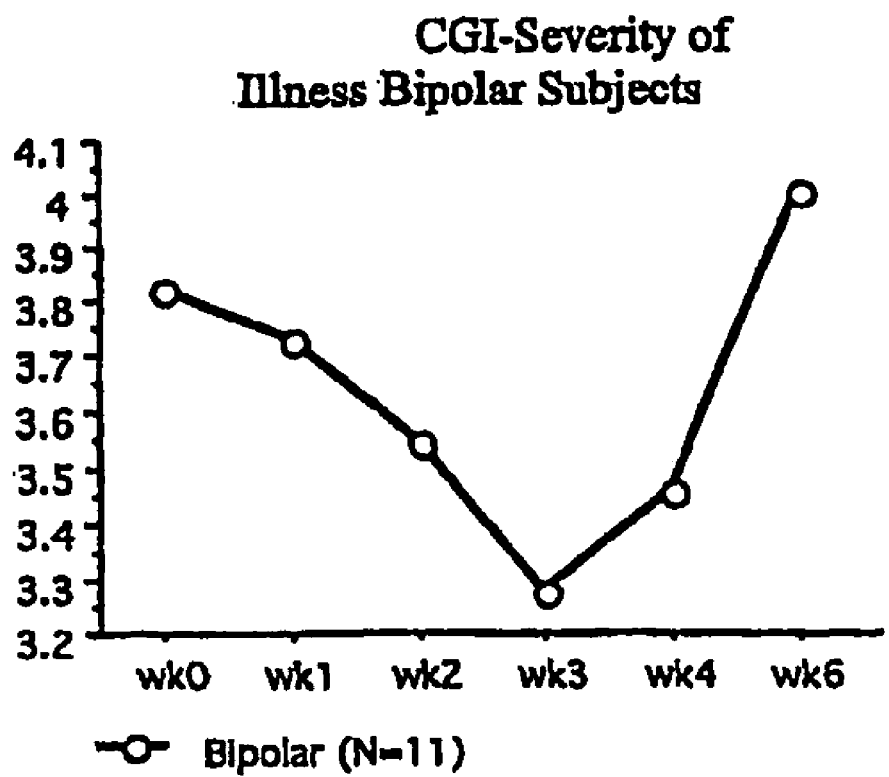
FIG. 3 is a graph showing the weekly Clinical Global Impression (CGI) scores of patients treated with uridine.

FIG. 3 shows that the CGI of bipolar patients in the study improved slightly from weeks one to three, and then deteriorated slightly from weeks three to six. At the end of the study, the average CGI score of the patient group was somewhat above baseline.

Example 3D

GAF

During the study patients were evaluated using Global Assessment of Functioning (GAF), which is a modified version of the Global Assessment Scale (GAS). The GAF is a single-item rating scale for evaluation of overall patient functioning during a specified period on a continuum from psychological or psychiatric illness to health. The scale value ranges from 1 (hypothetically sickest person) to 100 (hypothetically healthiest person), divided into 10 equal intervals.

Figure 4:
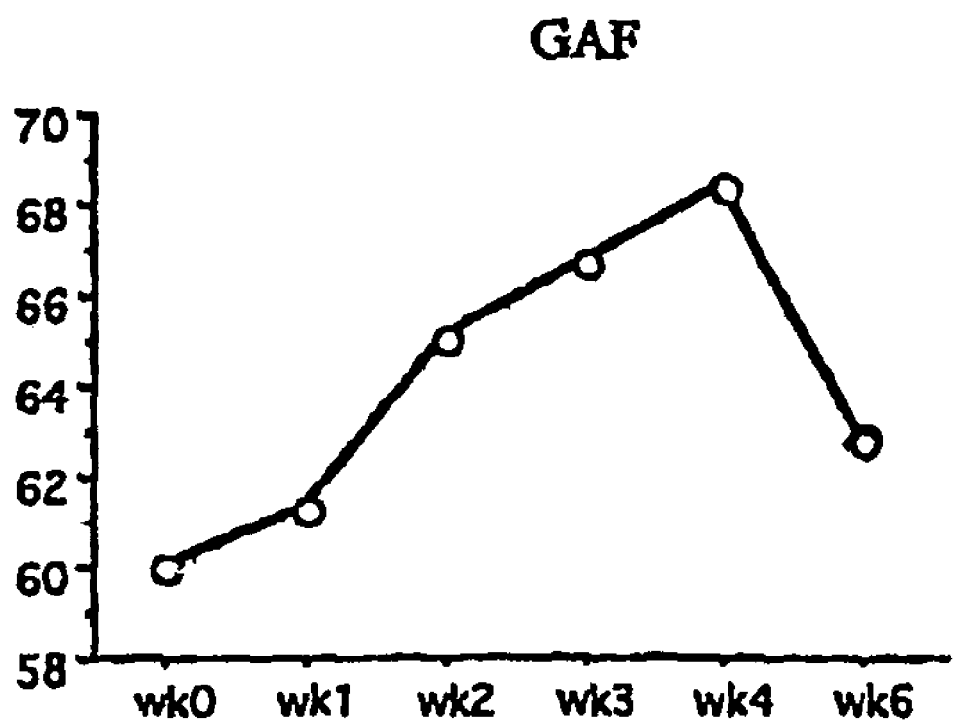
FIG. 4 is a graph showing the weekly Global Assessment of Functioning (GAF) scores of patients treated with uridine.

FIG. 4 shows that the average GAF score improved slightly from the beginning of the study to the week four, and then declined to a level slightly above the initial GAF score.

Example 3E

HAM-A

In another aspect of the study, patients were evaluated using the Hamilton Anxiety (HAM-A) rating scale. This scale measures the severity of symptoms such as anxiety, tension, depressed mood, palpitations, breathing difficulties, sleep disturbances, restlessness, and other physical symptoms. The HAM-A was one of the first rating scales developed to measure the severity of anxiety symptomatology, and is a widely used outcome measure in clinical trials. Mild Anxiety is indicated by a score of 18, moderate anxiety by a score of 25, and severe anxiety by a score of 30.

Figure 5:
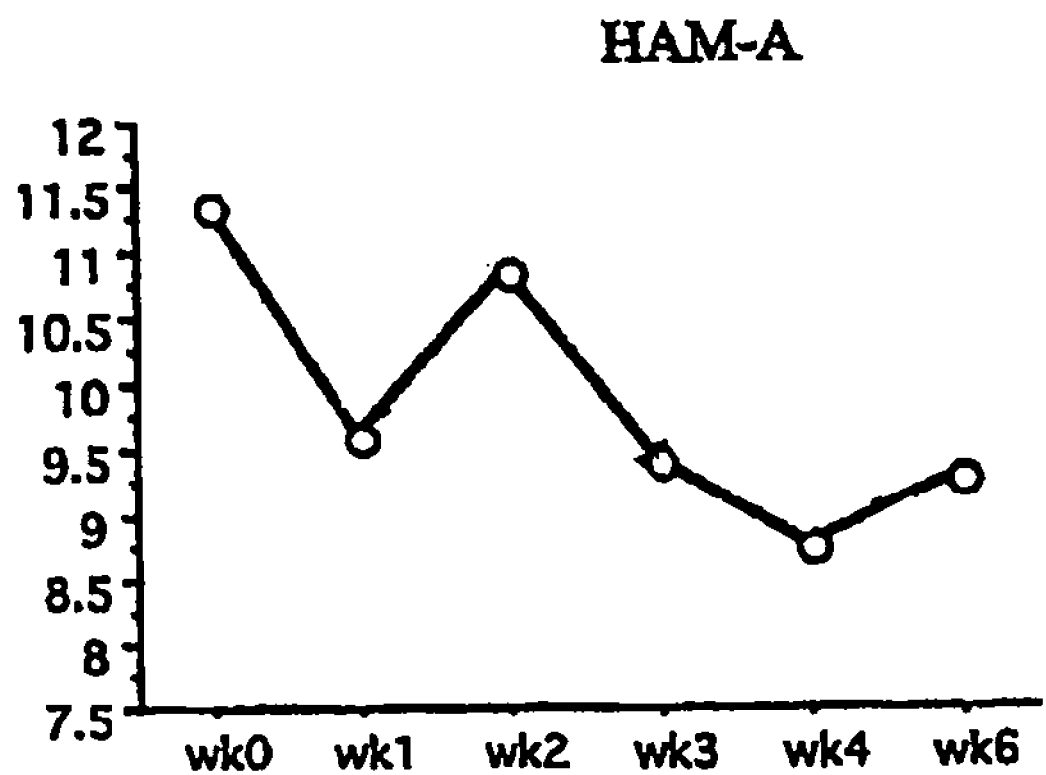
FIG. 5 is a graph showing the weekly Hamilton Anxiety (HAM-A) scores of patients treated with uridine.

FIG. 5 shows that the average HAM-A score in the patient group went down slightly during the course of the study.

Example 3F

YMRS by Gender

Figure 6:
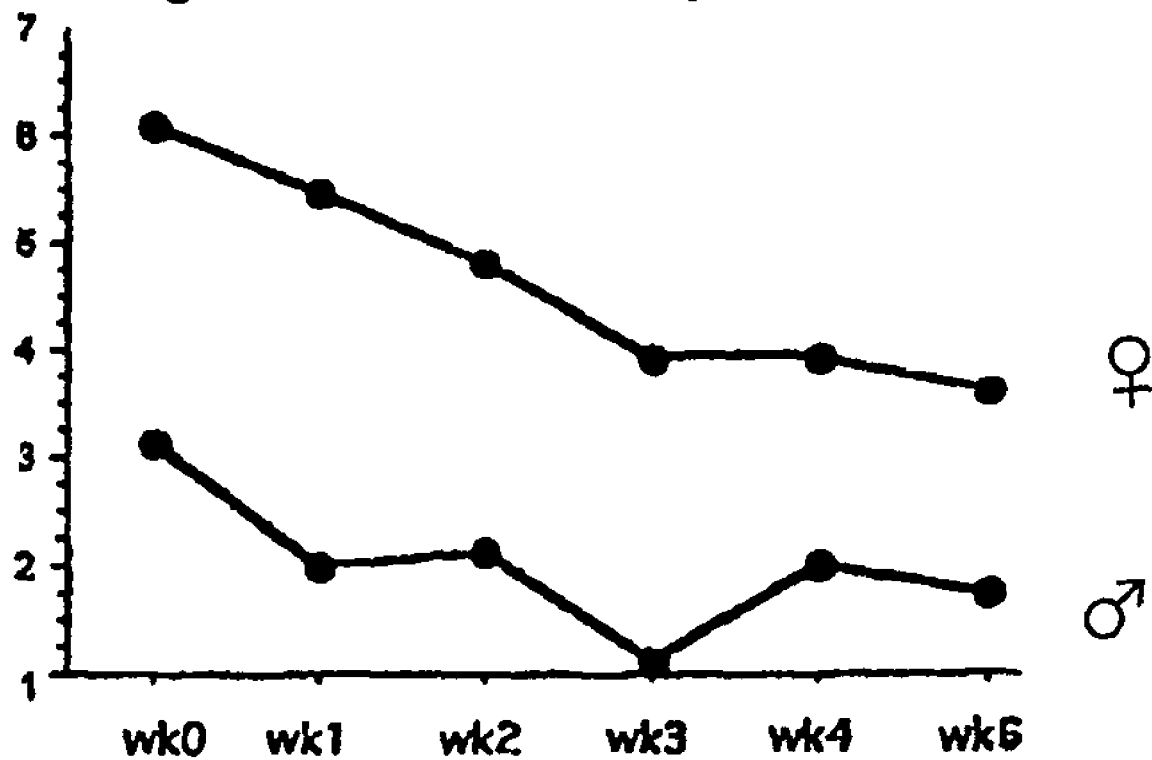
FIG. 6 is a graph showing the weekly YMRS scores of patients treated with uridine, divided according to gender.

FIG. 6 shows the average YMRS scores of patients in the study divided according to gender. The average YMRS for female patients declined slightly more than males YMRS scores during the first three weeks of the study. Female YMRS scores also did not increase above the initial baseline score during the study.

Example 3G

CGI by Gender

Figure 7:
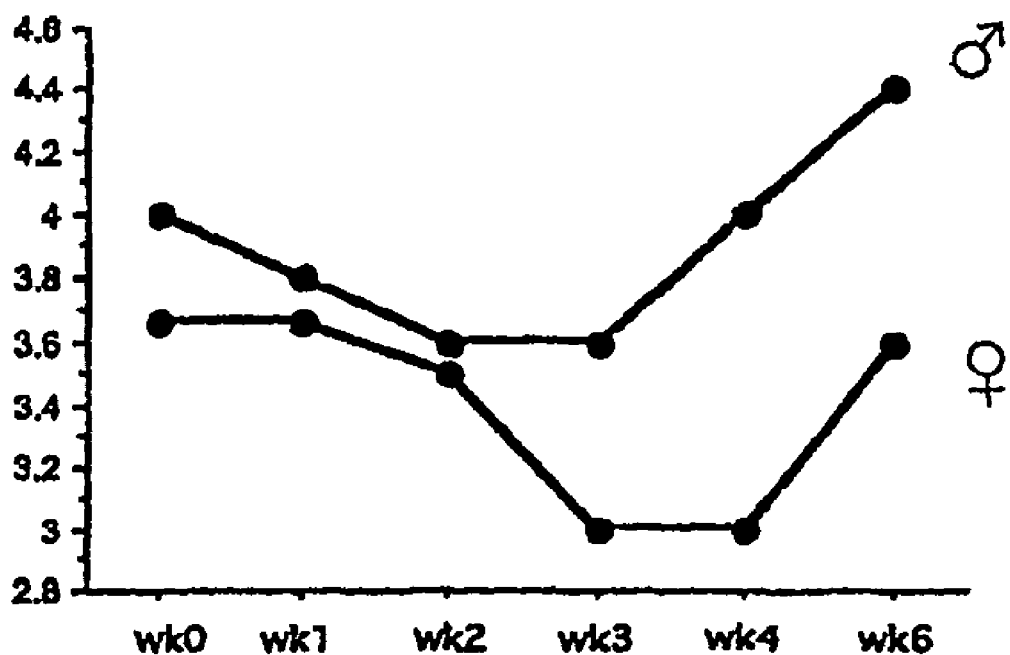
FIG. 7 is a graph showing the weekly CGI scores of patients treated with uridine, divided according to gender.

FIG. 7 shows the average CGI scores of patients in the study divided according to gender. Unlike average male CGI scores, average female CGI scores improved (i.e. declined) during the course of the study, relative to the initial score.

Example 3H

CGI by Antidepressant Medication

Figure 8:
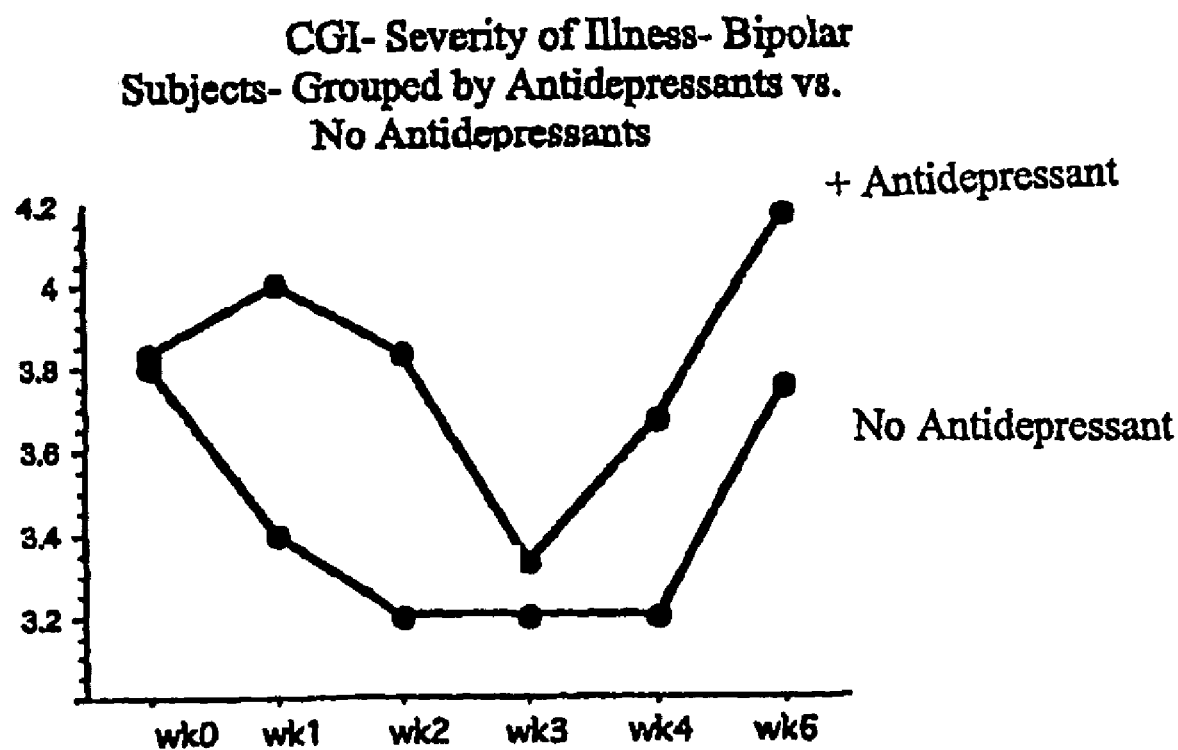
FIG. 8 is a graph showing the weekly CGI scores of patients treated with uridine, divided into groups of patients taking, or not taking, antidepressant medication.

FIG. 8 shows the average CGI for patients in the study divided according to whether the patient was taking an antidepressant medication. The group of patients that were not taking antidepressant exhibited a faster decline in average CGI scores than the group of patients who were on antidepressant medication.

Example 4

Adverse Events

The total number of adverse events is reported by the number and percentage of subjects experiencing each adverse event. If a subject reported the same adverse event over the course of the study, that event was counted once.

During the course of the 6-week study, there were some reported side effects to the medication. 1 subject reported stomach cramps, 1 reported nausea, 4 reported decreased appetite, 3 reported an increase in constipation, 4 reported diarrhea, 1 reported muscle cramps, 2 reported headaches, 1 reported fatigue, 2 reported problems with sleeping, 2 reported increased flatulence, and 1 reported a decrease in libido. In addition, one subject reported changes in her vision that affected her depth perception. Another subject reported "weaker vision." One subject dropped out of the study after the baseline visit and was unavailable for further questioning. One subject reported a manic episode during week 3 after reducing the dose of TAU treatment per the Principal Investigator's suggestion. The subject independently decided to increase her dose back to its original amount in response to her manic reaction to the decreased dose. Due to this protocol deviation, and the subject's manic break, the subject was terminated from the study.

Example 5

Clinical Study of Uridine Therapy in Bipolar Disorders

This study evaluates the therapeutic effects of uridine in subjects with a bipolar disorder and its ability to normalize altered bioenergetic markers in those subjects.

In addition to behavioral assessments, the subjects undergo a baseline MRI/MRS study followed by lithium monotherapy for four weeks. After four weeks of lithium monotherapy, subjects undergo repeat MRI/MRS studies are then divided into two groups: one receiving uridine in addition to lithium, and the other group receiving paroxetine in addition to lithium. Paroxetine is a selective serotonin reuptake inhibitor (SSRI) that has been extensively documented to be an effective and well-tolerated antidepressant treatment, and serves as a positive control in this study. By comparing the therapeutic effects of both uridine and paroxetine, which have very different mechanisms of action, in a double blind fashion, we can evaluate the therapeutic efficacy of uridine compared to paroxetine, as well as the relationship between brain changes in bioenergetics and treatment specific mood enhancement.

Clinical Methods—Treatment Protocol: Paroxetine vs. Uridine Randomized Treatment Following Lithium Stabilization Bipolar subjects undergo a baseline MRI/MRS study followed by Li monotherapy for four weeks. Dosing is initiated using a 600 mg test dose with subsequent dosing based on the next day trough serum Li level. After the initial dosage adjustment, a trough Li level is checked the following week to adjust dosage, as necessary, to achieve a serum level of 0.5 to 0.8 mEq/L. This range of therapeutic serum levels for mood stabilization is based on work suggesting a specific Li antidepressant effect above 0.8 mEq/L and to minimize adverse side effects (Nemeroff et al., 2001, Am. J. Psychiatry, 158(6): 906-912). After four weeks of Li monotherapy, subjects undergo repeat MRI/MRS studies and are then randomized with respect to supplemental double-blind treatment with paroxetine or uridine. Uridine is initiated and maintained at 1 gram twice a day, based on our experience in our preliminary treatment studies (described in Example 3).

Paroxetine is initiated at 20 mg/day (10 mg twice a day to maintain double-blind) with further dose adjustments during the first four weeks as clinically warranted based on therapeutic response and emergent side-effect profile. The aim is to maintain consistent dosing of paroxetine at a range between 20 mg to 50 mg/day (maximum dose based on clinical response parameters) for the final four weeks of the study. Due to potential withdrawal symptoms from abrupt discontinuation, at study conclusion, for patients that discontinue paroxetine, the drug is tapered at 10 to 20 mg per week as clinically tolerated. To monitor compliance with study medication, subjects are asked to keep a weekly medication diary.

Subject Recruitment

A total of 130 medication-free bipolar depressed individuals (26/year) are recruited and enrolled to end up with 110 bipolar subjects who have completed three scans, assuming a 15% treatment drop-out rate. In addition, twelve healthy controls are also enrolled each year for comparison scans. Individuals who respond to recruitment efforts (physician referrals, advertising) undergo an initial phone screen to determine likelihood of meeting study criteria. Those individuals who appear to meet study criteria are invited into the clinic for a screening interview. Upon arrival at the clinic, informed consent is obtained. Those individuals who provide consent undergo a psychiatric evaluation that includes the SCID-IV for Axis I, HAM-D; MADRS; and YES. These scales are chosen as they are standard assessment tools for mood with known reliability. Individuals who meet study criteria then undergo a screening review of systems, past medical history, physical examination, and laboratory testing (complete blood count (CBC); standard blood screening battery, including electrolytes, liver function tests and Bun/Creatine; T4 and thyroid stimulating hormone (TSH); ECG; urine HCG; and urine toxic screen).

Inclusion Criteria: aged 18 to 40 years; DSM-IV criteria met for Bipolar Disorder-depressed; HAM-D score >18, and YMRS score <7; psychotropic medication-free for at least two months; capable of providing informed consent; and has an established residence and phone.

Exclusion Criteria: meets DSM-IV criteria for another Axis I disorder, except co-morbid anxiety disorder or history of substance abuse disorder; alcohol or substance dependence or actively abusing within the past month; co-morbid medical condition which in the opinion of the investigator contributes to the individual's mood symptoms (stable and adequately treated thyroid disease will be permitted); acutely suicidal or moderate to high suicide risk; women of child-bearing potential who are unwilling to use a standard method of birth control for the duration of the study; pregnancy or breast-feeding; allergy or other contraindication to paroxetine, uridine or Li; history of significant head trauma; claustrophobia or other contraindication to MRI (e.g., pacemaker, metal fragments).

Schedule of Visits

The following treatment schedule is used.

Week 0; Visit 1: Screening psychiatric/medical workup as described above; informed consent; SCID-IV for Axis I; rating scales: HAM-D, MADRS, YMRS and clinician global impression.

Week 1; Visit 2: Baseline MR exam (before starting treatment); review laboratory results; repeat rating scales; Bipolar subjects only—Dispense Li with single 600 mg dose then next day blood level (Visit 3), followed by Li adjustment to establish serum Li levels between 0.5-0.8 mEq/L.

Week 2; Visit 4: Bipolar subjects only—Repeat Li blood level; clinical assessment (including clinician and patient global improvement scales and adverse event monitoring); rating scales.

Week 4; Visit 5: Rating scales; repeat urine HCG and toxic screen; repeat MRS scan. Bipolar subjects only—Clinical assessment; repeat Li blood level; subjects randomized into double-blind supplemental treatment with paroxetine 10 mg twice a day or uridine 1 gram twice a day.

Weeks 5-8; Visits 6 thru 8: Bipolar subjects only—Clinical assessment; rating scales.

Week 10; Visit 9: Bipolar subjects only—Clinical management; rating scales.

Week 12; Visit 10: Bipolar subjects only—Clinical management; rating scales; repeat urine HCG and toxic screen; repeat MRI/MRSI scanning.

Week 13; Visit 11 (Follow-up): Bipolar subjects only—Clinical assessment. Repeat medical workup, transition off of uridine (and taper paroxetine if patient requests discontinuation). Refer for follow-up treatment.

Early Termination: Individuals who decide to terminate early from the study or whose condition worsens during the study such that they are in need of more intensive treatment than that provided by the study are asked to return to the clinic for an early termination visit. Individuals are evaluated and triaged according to their clinical needs. Study medications are discontinued and repeat rating scales, laboratory studies, and physical exam are obtained to the extent that the subject is able to cooperate. If an individual enrolled in the study has an emergency or acute decompensation, appropriate treatment is found for this individual prior to termination.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an individual exhibiting one or more symptoms of bipolar disorder, the method comprising administering to the individual a therapeutically-effective amount of a uridine composition that provides 1 to 7 grams of uridine per day.

2. The method of claim 1, wherein the therapeutically-effective amount of the uridine composition provides 2 to 5 grams of uridine per day.

3. The method of claim 1, wherein the therapeutically-effective amount of the uridine composition provides 3 to 4 grams of uridine per day.

4. The method of claim 1, wherein the individual is diagnosed under DSM-IV guidelines as having bipolar disorder.

5. The method of claim 1, wherein the composition is administered in two or three doses/day.

6. The method of claim 1, wherein the composition is triacetyl uridine, uridine monophosphate, uridine diphosphate, or uridine triphosphate.

7. The method of claim 1, wherein the uridine composition is administered orally.

8. The method of claim 1, wherein the individual is suffering from type I bipolar disorder.

9. The method of claim 1, wherein the individual is suffering from type II bipolar disorder.

10. The method of claim 1, wherein the therapeutically-effective amount of the uridine composition is an amount sufficient to improve one or more symptoms of bipolar disorder.

11. The method of claim 10, wherein the symptoms are one or more symptoms of a major depressive episode.

12. The method of claim 10, wherein the symptoms are one or more symptoms of a manic episode.

13. The method of claim 10, wherein the symptoms are one or more symptoms of a mixed episode.

14. The method of claim 10, wherein the symptoms are one or more symptoms of a hypomanic episode.

15. A method of reducing anxiety in an individual suffering from bipolar disorder, the method comprising administering to the individual a therapeutically-effective amount of a uridine composition that provides 1 to 7 grams of uridine per day.

16. A method of reducing the severity of manic symptoms in an individual in need of treatment for bipolar disorder, the method comprising administering to the individual a therapeutically-effective amount of a uridine composition that provides 1 to 7 grams of uridine per day.

17. The method of claim 1, wherein the uridine composition is uridine.

18. The method of claim 15, wherein the uridine composition is uridine.

19. The method of claim 16, wherein the uridine composition is uridine.

* * * * *